(12) United States Patent
Wada et al.

(10) Patent No.: US 8,101,073 B2
(45) Date of Patent: Jan. 24, 2012

(54) SEPARATING AGENT FOR SOLID-PHASE EXTRACTION

(75) Inventors: Hiroo Wada, Fushimi-ku (JP); Kosuke Fukuzawa, Fushimi-ku (JP)

(73) Assignee: Shinwa Chemical Industries, Ltd., Kyoto (JP)

( * ) Notice: Subject to any disclaimer, the term of this patent is extended or adjusted under 35 U.S.C. 154(b) by 1569 days.

(21) Appl. No.: 11/215,024

(22) Filed: Aug. 31, 2005

(65) Prior Publication Data
US 2006/0043022 A1    Mar. 2, 2006

(30) Foreign Application Priority Data
Aug. 31, 2004  (JP) .................................. 2004-252612

(51) Int. Cl.
*B01D 15/08* (2006.01)

(52) U.S. Cl. .................. 210/198.2; 210/502.1; 210/635; 210/656

(58) Field of Classification Search ............... 210/502.1, 210/634, 635, 656, 659, 198.2; 96/101; 502/402
See application file for complete search history.

(56) References Cited

U.S. PATENT DOCUMENTS

| | | | |
|---|---|---|---|
| 4,140,653 A | | 2/1979 | Imura et al. |
| 4,544,485 A * | 10/1985 | Pinkerton et al. ......... 210/502.1 |
| 4,725,359 A * | 2/1988 | Ray ............... 210/640 |
| 4,920,152 A * | 4/1990 | Regnier et al. .............. 521/31 |
| 5,030,352 A * | 7/1991 | Varady et al. ............ 210/502.1 |
| 5,182,016 A * | 1/1993 | Funkenbusch et al. .... 210/198.2 |
| 5,200,069 A * | 4/1993 | Lin ............ 210/198.2 |
| 5,205,929 A * | 4/1993 | Carr et al. ............ 210/198.2 |
| 5,230,806 A * | 7/1993 | Fritz et al. ............ 210/692 |
| 5,277,813 A * | 1/1994 | Feibush et al. ............ 210/502.1 |
| 5,503,933 A * | 4/1996 | Afeyan et al. ............ 428/407 |
| 5,519,064 A * | 5/1996 | Stringfield et al. ............ 521/54 |
| 5,773,587 A * | 6/1998 | Lowe et al. ............ 530/413 |
| 5,876,605 A * | 3/1999 | Kitajima et al. ............ 210/650 |
| 5,906,747 A * | 5/1999 | Coffman et al. ............ 210/635 |
| 6,039,876 A * | 3/2000 | Yang ............ 210/635 |
| 6,045,697 A * | 4/2000 | Girot et al. ............ 210/635 |

(Continued)

FOREIGN PATENT DOCUMENTS

JP         5-302917        11/1993

(Continued)

OTHER PUBLICATIONS

Kunio Furusawa, et al., "Syntheses of Composite Polystyrene Latices with Silica Particles in the Core", Journal of Colloid and Interface Science, vol. 109, No. 1, Jan. 1986, pp. 69-76.

*Primary Examiner* — Ernest G Therkorn
(74) *Attorney, Agent, or Firm* — Oblon, Spivak, McClelland, Maier & Neustadt, L.L.P.

(57) ABSTRACT

The present invention relates to a separating agent for solid-phase extraction which comprises core particles of a base material; a hydrophilic polymer layer formed on the surface of the particles; and a hydrophobic polymer layer formed on the surface of the hydrophilic polymer layer. The separating agent can be used in a cartridge or a column for solid-phase extraction and the latter can in turn be used in a variety of methods such as a method for concentrating a subject to be separated; a method for removing impurities; a method for solid-phase extraction of an environmental, medicinal and/or biological samples; and a method for pre-treating a protein component-containing sample.

11 Claims, 1 Drawing Sheet

U.S. PATENT DOCUMENTS

| | | | |
|---|---|---|---|
| 6,322,695 B1 * | 11/2001 | Lee et al. | 210/198.2 |
| 6,413,621 B1 * | 7/2002 | Mayes et al. | 428/212 |
| 6,773,583 B2 * | 8/2004 | Bouvier et al. | 210/198.2 |
| 7,232,520 B1 * | 6/2007 | Lee et al. | 210/198.2 |
| 2005/0029196 A1 * | 2/2005 | Rhemrev-Boom | 210/656 |
| 2007/0084788 A1 * | 4/2007 | Moya et al. | 210/500.29 |

FOREIGN PATENT DOCUMENTS

| | | |
|---|---|---|
| JP | 6-258203 | 9/1994 |
| JP | 8-325428 | 12/1996 |
| JP | 2000-26551 | 1/2000 |
| JP | 3055911 | 4/2000 |
| JP | 2000-514704 | 11/2000 |
| JP | 2001-343378 | 12/2001 |
| JP | 2002-139482 | 5/2002 |
| JP | 2002-517574 | 6/2002 |
| WO | WO 97/38774 | 10/1997 |
| WO | WO 99/64480 | 12/1999 |
| WO | WO 01/59444 | 8/2001 |

* cited by examiner

SEPARATING AGENT FOR SOLID-PHASE EXTRACTION

BACKGROUND OF THE INVENTION

The present invention relates to a separating agent for solid-phase extraction; a column or cartridge for solid-phase extraction using the separating agent; a method for concentrating a subject to be separated; a method for removing impurities; a method for solid-phase extraction of an environmental, medicinal and/or biological samples; and a method for pre-treating a protein component-containing sample. These methods make use of the column or cartridge packed with the separating agent.

The solid-phase extraction method means a physical extraction process in which a liquid and a solid are concerned. In the solid-phase extraction technique, when the affinity of a substance to be separated for a solid phase is, for instance, greater than that of the substance to be separated for the solvent in which the substance is dissolved (sample solution) and when the sample solution passes through the solid phase bed, the substance is concentrated on the surface of the solid phase, while other components present in the sample solution pass through the solid phase bed. Thus, the target substance can be separated. Contrary to the foregoing method, there has been known a method in which the target substance can pass through a solid phase bed, while other components of the sample solution are fixed onto the solid phase to thus separate the same. As separating agents used in the solid-phase extraction technique, there have been known, for instance, inorganic base materials such as silica gel or chemically modified silica gel obtained by chemically modifying the surface of silica gel particles; and organic base materials such as synthetic polymer type ones represented by styrene-divinyl benzene copolymers and those obtained by chemically modifying the surface of these organic base materials.

In general, the synthetic polymeric base material used in the chromatography technique is constituted by a large number of discrete particles having a large number of fine pores of a small depth distributed on the surface thereof and having a regular shape, preferably a spherical shape.

In most of cases, the synthetic polymeric base material is prepared according to the suspension polymerization technique since this technique is quite simple to handle and it is excellent in the reproducibility. In general, the resulting polymer particles are subjected to an appropriate classification treatment to thus obtain only a product having a particle size favorably used as a material which is packed into a column for chromatography (packing material) (see, for instance, Patent Documents Nos. 1 to 11 and Non-Patent Document 1 listed below):

Patent Documents No. 1: JP-A-2002-139482
Patent Documents No. 2: JP-A-2001-343378
Patent Documents No. 3: JP-A-Hei 6-258203
Patent Documents No. 4: JP-A-2000-514704
Patent Documents No. 5: JP-A-2002-517574
Patent Documents No. 6: JP-A-Hei 5-302917
Patent Documents No. 7: WO01/059444
Patent Documents No. 8: Japanese Patent No. 3,055,911
Patent Documents No. 9: JP-A-2000-26551
Patent Documents No. 10: JP-A-Hei 8-325428
Patent Documents No. 11: U.S. Pat. No. 4,140,653B
Non-Patent Document 1: KUNIO FURUSAWA et al., "Syntheses of Composite Polystyrene Latices with Silica Particles in the Core", Journal of Colloid and Interface Science, 1986, Vol. 109, No. 1.

SUMMARY OF THE INVENTION

The styrene-divinyl benzene copolymers listed above as examples of the foregoing synthetic polymeric base materials are strongly hydrophobic in nature and the copolymers accordingly suffer from a problem in that the workability becomes insufficient when handling the aqueous solution thereof. In addition, the styrene-divinyl benzene copolymers get swollen and/or undergo shrinkage depending on solvents used and therefore, it would be required for the use of a complicated extraction method in which the kinds of solvents to be used should frequently be changed. For this reason, there has been desired for the development of a base material having hydrophilicity and hydrophobicity in combination.

In most of commercially available synthetic polymeric base materials, the base materials per se are constituted by polymer particles. It would be quite ideal that these polymer particles have regular surface in order to realize a chromatograph or a chromatographic column having high reproducibility.

The synthetic polymeric base material serving as a separating agent is in general prepared according to suspension polymerization, but it has been known that particles prepared by this polymerization method have a quite wide particle size distribution. For this reason, a yield of particles suitably used as a separating agent for chromatography is quite low and the separating agent would thus be liable to be quite expensive. Accordingly, there has been desired for the development of a separating agent for chromatography, which can maintain the desired quality peculiar to such a polymeric base material and a method for preparing the same at low cost.

Accordingly, it is an object of the present invention to provide a separating agent for solid-phase extraction, which has hydrophilicity and hydrophobicity in combination and a narrow particle size distribution, and which can be prepared at a high yield and at low cost.

It is another object of the present invention to provide a column or a cartridge which is packed with the foregoing separating agent for solid-phase extraction.

It is a further object of the present invention to provide a method for concentrating a subject to be separated; a method for removing impurities; a method for solid-phase extraction of an environmental, medicinal and/or biological samples; and a method for pre-treating a protein component-containing sample, these method being characterized in that they use the foregoing separating agent for solid-phase extraction.

According to the present invention, there are thus provided a separating agent for solid-phase extraction, a column or cartridge which is packed with the same and a method using the same as will be detailed below:

1. A separating agent for solid-phase extraction comprising core particles of a base material; a hydrophilic polymer layer formed on the surface of the particles; and a hydrophobic polymer layer formed on the surface of the hydrophilic polymer layer.

2. The separating agent for solid-phase extraction according to the foregoing item 1, wherein the hydrophilic polymer is at least one member selected from the group consisting of hydroxypropyl cellulose, methyl cellulose and ethyl cellulose.

3. The separating agent for solid-phase extraction according to the foregoing item 1 or 2, wherein the hydrophobic polymer comprises a polymer of a hydrophobic, crosslinkable monomer (A); a copolymer of a hydrophobic, crosslinkable monomer (A) and a hydrophobic, non-crosslinkable monomer (B); a copolymer of a hydrophobic, crosslinkable monomer (A) and a hydrophilic monomer (C); or a copolymer of a hydrophobic, crosslinkable monomer (A), a hydrophobic, non-crosslinkable monomer (B) and a hydrophilic monomer (C).

4. The separating agent for solid-phase extraction according to the foregoing item 3, wherein the hydrophobic, crosslinkable monomer (A) is at least one member selected from the group consisting of di-(meth)acrylic acid esters, poly(meth) acrylic acid esters of polyhydric alcohols, and aromatic compounds carrying at least two vinyl groups.

5. The separating agent for solid-phase extraction according to the foregoing item 3 or 4, wherein the hydrophobic, non-crosslinkable monomer (B) is at least one member selected from the group consisting of (meth)acrylic acid esters, vinyl carboxylate and styrenic monomers.

6. The separating agent for solid-phase extraction according to any one of the foregoing items 3 to 5, wherein the hydrophilic monomer (C) is at least one member selected from the group consisting of (meth)acrylic acid esters, (meth)acrylamides, and N-vinyl pyrrolidone, which have hydroxyl groups.

7. The separating agent for solid-phase extraction according to any one of the foregoing items 3 to 6, wherein the hydrophobic, crosslinkable monomer (A) is divinyl benzene.

8. The separating agent for solid-phase extraction according to any one of the foregoing items 3 to 6, wherein the hydrophobic, non-crosslinkable monomer (1) is styrene.

9. The separating agent for solid-phase extraction according to any one of the foregoing items 1 to 8, wherein the total amount of the hydrophobic polymer layer ranges from 5 to 500 parts by mass, per 100 parts by mass of the total amount of the core particles of the base material and the hydrophilic polymer layer.

10. The separating agent for solid-phase extraction according to any one of the foregoing items 1 to 9, wherein the core particles of the base material are at least one member selected from the group consisting of silica gel particles, cellulose particles, agarose particles, ceramic particles, carbon particles and synthetic polymer particles.

11. The separating agent for solid-phase extraction according to any one of the foregoing items 1 to 10, wherein the separating agent has an average particle size ranging from 1 to 200 µm.

12. A column or cartridge packed with a separating agent for solid-phase extraction according to any one of the foregoing items 1 to 11.

13. A method for concentrating a substance to be separated, the method being characterized in that it uses a separating agent for solid-phase extraction according to any one of the foregoing items 1 to 11.

14. A method for removing impurities, the method being characterized in that it uses a separating agent for solid-phase extraction according to any one of the foregoing items 1 to 11.

15. A method for solid-phase extraction of an environmental, medicinal or biological sample, the method being characterized in that it uses a separating agent for solid-phase extraction according to any one of the foregoing items 1 to 11.

16. A method for pre-treating a protein component-containing sample, the method being characterized in that it uses a separating agent for solid-phase extraction according to any one of the foregoing items 1 to 11.

The separating agent for solid-phase extraction according to the present invention comprises core particles of a base material; a hydrophilic polymer layer formed on the surface of the particles; and a hydrophobic polymer layer formed on the surface of the hydrophilic polymer layer and therefore, it simultaneously possesses hydrophilicity and hydrophobicity. For this reason, the workability is quite excellent when handling the aqueous solution of the separating agent and the agent would hardly get swollen and undergo shrinkage due to the action of a solvent used. Moreover, the separating agent contains a hydrophilic polymer layer and a hydrophobic polymer layer formed on the surface of core particles of a base material. Accordingly, the particle size distribution of the separating agent can easily be controlled, the yield thereof can be improved and the agent can be prepared at low cost.

BEST MODE FOR CARRYING OUT THE INVENTION

Figure 1:
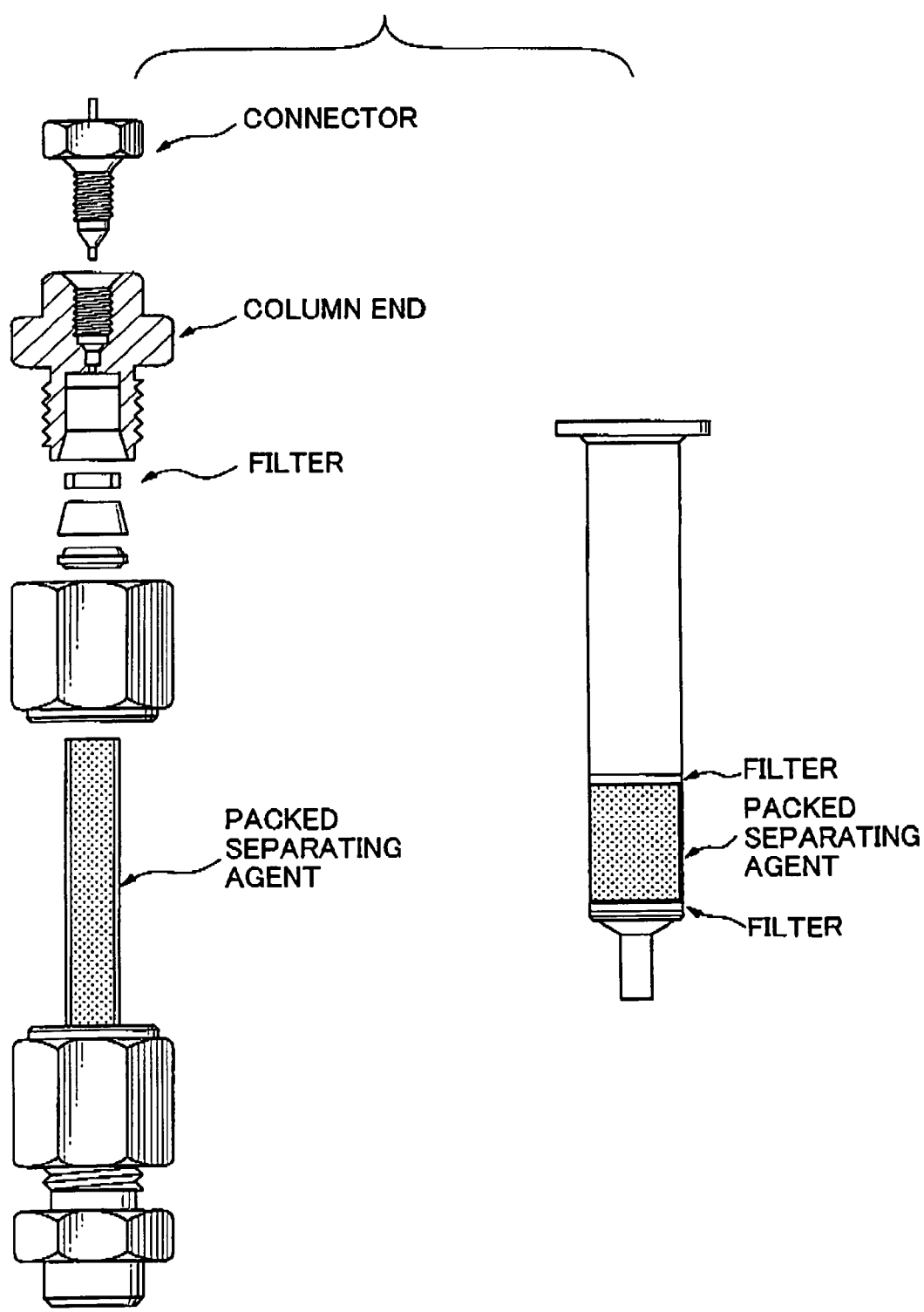
FIG. 1 shows schematic sectional side elevations illustrating a column deft side) and a cartridge (right side) suitably used herein while they are packed with the separating agent for solid-phase extraction according to the present invention.

The core particles of a base material used in the present invention may be particles of, for instance, silica gel, cellulose, agarose, ceramic, carbon and synthetic polymer. The particle size of the core particles preferably ranges from 1 to 200 µm and more preferably 30 to 80 µm.

The hydrophilic polymer used in the present invention may be, for instance, a polymer carrying hydrophilic groups such as hydroxyl groups and having a molecular weight ranging from 1000 to 2,000,000. Specific examples thereof are cellulose derivatives such as methyl cellulose, ethyl cellulose and hydroxypropyl cellulose; polyvinyl pyrrolidone; and hexadimethrine bromide(polybrene).

Regarding the bonding of the hydrophilic polymer to the surface of the core particles of the base material, in the present invention, the hydrophilic polymer does not substantially form any linkage with the core particles within the fine pores of the particles and therefore, the linkage of the hydrophilic polymer with the surface of the core particles means that the former is physically or chemically bonded to the outer surface of the latter.

In the present invention, the functional groups of the hydrophilic polymer may be partially or completely be subjected to chemical modification. The chemical modification herein used means, for instance, the conversion thereof into a diol; reduction; or the conversion thereof into a glutaryl derivative. The conversion into a diol herein means, for instance, a reaction for forming two hydroxyl groups by treating the cyclic portion of a methacryloxy ring with an acid such as a diluted sulfuric acid solution.

In the present invention, the coated amount of the hydrophilic polymer preferably ranges from 0.01 to 1000 parts by mass and more preferably 0.1 to 10 parts by mass, per 100 parts by mass of the core particles of the base material.

As materials for forming the hydrophobic polymer layer, there may be listed, for instance, those comprising a polymer of a hydrophobic, crosslinkable monomer (A); a copolymer of a hydrophobic, crosslinkable monomer (A) and a hydrophobic, non-crosslinkable monomer (B); a copolymer of a hydrophobic, crosslinkable monomer (A) and a hydrophilic monomer (C); or a copolymer of a hydrophobic, crosslinkable monomer (A), a hydrophobic, non-crosslinkable monomer (B) and a hydrophilic monomer (C).

Examples of the hydrophobic, crosslinkable monomers (A) include di(meth)-acrylic acid esters such as ethylene glycol di(meth)acrylate, polyethylene glycol di-(meth)acrylate, propylene glycol di(meth)acrylate and polypropylene glycol di(meth)-acrylate; poly(meth)acrylic acid esters of polyhydric alcohols such as tetra-methylol methane tri(meth)acrylate and tetra-methylol methane tetra(meth)acrylate; and aromatic compounds carrying at least two vinyl groups such as divinyl benzene, divinyl toluene and divinyl naphthalene.

Preferred hydrophobic, crosslinkable monomer (A) is divinyl benzene because of its easy availability. The amount of the hydrophobic, crosslinkable monomer (A) present in the foregoing copolymer preferably ranges from 20 to 95% by mass on the basis of the total mass of the monomers (A), (B) and (C) as expressed in terms of the charged amount thereof while taking into consideration the intended hydrophobicity and more preferably not less than 40% by mass while taking into consideration the swelling and shrinkage of the resulting copolymer. In addition, it is preferred that the divinyl benzene used herein preferably has a purity of not less than 80%.

Examples of hydrophobic, non-crosslinkable monomers (B) usable herein are (meth)acrylic acid esters such as methyl (meth)acrylate, ethyl (meth)acrylate, propyl (meth)acrylate, butyl (meth)acrylate and t-butyl (meth)acrylate; vinyl carboxylates such as vinyl acetate and vinyl propionate; and styrenic monomers such as styrene, methyl styrene, chloromethyl styrene and butoxy styrene.

Preferred hydrophobic, non-crosslinkable monomer (B) is styrene because of its easy availability. The amount of the hydrophobic, non-crosslinkable monomer (B) present in the foregoing copolymer preferably ranges from 5 to 80% by mass on the basis of the total mass of the monomers (A), (B) and (C) and more preferably 5 to 60% by mass as expressed in terms of the charged amount thereof, while talking into consideration the swelling and shrinkage of the resulting copolymer.

Examples of hydrophilic monomers (C) are unsaturated carboxylic acids such as (meth)acrylic acid, itaconic acid and maleic acid; (meth)acrylic acid esters carrying, for instance, hydroxyl groups, amino groups and/or ether groups such as hydroxyethyl (meth)acrylate, hydroxypropyl (meth)acrylate, polyethylene glycol (meth)acrylate, 2,3-dihydroxypropyl (meth)acrylate, glycosyl ethyl (meth)acrylate, dimethyl-aminoethyl (meth)acrylate, diethyl-aminoethyl (meth)acrylate and tetrahydro-furfuryl (meth)-acrylate; (meth)acrylic acid amides such as (meth)acrylamide, N,N-dimethyl (meth)-acrylamide and dimethyl-aminopropyl (meth)acrylamide; vinyl ethers such as methyl vinyl ether and ethyl vinyl ether; allyl alcohols; N-vinyl heterocyclic compounds such as N-vinyl pyridine and N-vinyl imidazole; and N-vinyl lactams such as N-vinyl piperidone, N-vinyl pyrrolidone and N-vinyl caprolactam. Among these hydrophilic monomers, preferably used herein are those having high hydrophilicity, for instance, (meth)acrylic acid esters carrying hydroxyl groups such as hydroxyethyl (meth)acrylate, hydroxy-propyl (meth)acrylate, polyethylene glycol (meth)acrylate, 2,3-dihydroxypropyl (meth)acrylate, glycosyl ethyl (meth)acrylate and allyl alcohol; and (meth)acrylamide, N-vinyl pyridine, N-vinyl piperidone, N-vinyl pyrrolidone and N-vinyl caprolactam, with (meth)-acrylic acid esters carrying hydroxyl groups, (meth)acrylamide, N-vinyl pyrrolidone or the like being more preferably used herein.

The amount of the hydrophilic monomer (C) present in the foregoing copolymer preferably ranges from 5 to 80% by mass on the basis of the total mass of the monomers (A), (B) and (C) and more preferably 5 to 60% by mass as expressed in terms of the charged amount thereof, while taking into consideration the swelling and shrinkage of the resulting copolymer.

In the present invention, the coated amount of the hydrophobic polymer layer preferably ranges from 5 to 500 parts by mass and more preferably 30 to 200 parts by mass, per 100 parts by mass of the core particles of the base material, which are coated with the foregoing hydrophilic polymer.

The separating agent for solid-phase extraction according to the present invention has a porous structure and therefore, a solvent for dilution is added to a monomer mixture used for forming such a hydrophobic polymer layer prior to the polymerization of the mixture for the purpose of imparting the desired porosity to the resulting polymer.

The solvent used for the dilution may be an organic solvent which can dissolve the monomer mixture, but is inert for the polymerization reaction and which never dissolves the resulting polymer. Specific examples of such solvents are aromatic hydrocarbons such as toluene, xylene, ethyl benzene and diethyl benzene; saturated hydrocarbons such as hexane, heptane, octane and decane; alcohols such as isoamyl alcohol, hexyl alcohol, octyl alcohol and 2-ethylhexyl alcohol; aliphatic halogenated hydrocarbons such as dichloromethane, dichloroethane and trichloroethane; and aliphatic or aromatic esters such as ethyl acetate, butyl acetate, dimethyl phthalate and diethyl phthalate. These organic solvents may be used alone or a mixture of at least two of them.

The amount of these dilution solvent to be added preferably ranges from 0.5 to 500 parts by mass and more preferably 1 to 300 parts by mass, per 100 parts by mass of the total amount of the monomers used for forming the hydrophobic polymer layer.

In the present invention, the hydrophobic polymer layer may be formed on the surface of the core particles of the base material, which has been coated with the foregoing hydrophilic polymer layer, by polymerizing a monomer (A), a mixture of a monomer (A) with a monomer (B), a mixture of a monomer (A) with a monomer (C), or a mixture of a monomer (A), a monomer (B) and a monomer (C), in the presence of the core particles of the base material, provided thereon with the hydrophilic polymer layer to thus coat the core layer with the hydrophobic polymer layer. The polymerization is preferably carried out according to the suspension polymerization technique in an aqueous medium containing an appropriate dispersant. In this case, a polymerization initiator is used, but may be any one insofar as it may be a known radical initiator capable of generating radicals. Specific examples thereof include organic peroxide type initiators such as benzoyl peroxide, dichloro-benzoyl peroxide, dicumyl peroxide, di-t-butyl peroxide and t-butyl perbenzoate, methyl ethyl ketone peroxide and methyl cyclohexanone peroxide; and azo type initiators such as 2,2'-azobis-isobutyronitrile and 2,2'-azobis-(2,4-dimethyl valeronitrile).

It is preferred to use the polymerization initiator in an amount ranging from 0.001 to 5 part by mass per 100 parts by mass of the total mass of the monomers (A), (B) and (C).

The polymerization reaction is carried out by stirring an aqueous phase containing an appropriate dispersant and an organic phase containing, for instance, monomers, a dilution solvent and a polymerization initiator. Such a dispersant usable herein may be any known one. Specific examples thereof are water-soluble polymeric compounds such as gelatin, sodium polyacrylate, polyvinyl alcohol, methyl cellulose, ethyl cellulose, hydroxypropyl cellulose and carboxymethyl cellulose. The concentration of the dispersant used preferably ranges from 0.001 to 5% by mass on the basis of the mass of the aqueous medium. The aqueous medium is a medium mainly comprising water and it may comprise salts and other water-soluble components dissolved therein, in addition to water.

The polymerization reaction in the present invention is carried out in the presence of an appropriate emulsifying agent and such an emulsifying agent usable herein may be any known one. Specific examples thereof are anionic surfactants such as dodecyl benzene sulfuric acid salts, dodecyl sulfuric acid salts, lauryl sulfuric acid salts, dialkyl sulfo-succinic acid salts, polyoxyethylene alkylphenyl ether sulfuric acid salts, polyoxyethylene alkyl propenyl-phenyl ether sulfuric acid salts and formalin-condensate of naphthalene sulfonic acid. In this respect, salts may be sodium salts and ammonium salts. It is also possible to use nonionic surfactants such as polyoxyethylene nonyl-phenyl ethers, polyethylene glycol monostearates, polyoxyethylene alkyl-propenyl phenyl ethers and sorbitan monostearate, as such emulsifying agents.

In the present invention, the hydrophobic polymer layer may be formed on the surface of the core particles of the base material, which has been coated with the foregoing hydrophilic polymer layer, by stirring in a nitrogen atmosphere, an organic phase containing, for instance, monomers required for the formation of such a hydrophobic polymer layer, an organic solvent and an initiator; and a liquid containing a dispersion phase of an aqueous medium in, for instance, a homogenizer at a rate ranging from 300 to 10,000 rpm and at a temperature ranging from 15 to 35° C., for instance, at room temperature to thus polymerize the monomer according to the suspension polymerization. After the confirmation of whether an emulsion is formed or not, the stirring speed is reduced to a level of 5 to 200 rpm, the core particles of the base material, which has been coated with the foregoing hydrophilic polymer layer, are added to the emulsion, followed by the polymerization reaction at a temperature ranging from 70 to 90° C. for not less than 20 hours in a nitrogen atmosphere. The particles prepared according to the foregoing steps are, if necessary, classified in such a manner that their particle size would fall within the range of from 1 to 200 µm and preferably 30 to 80 µm and then they are used as a separating agent for solid-phase extraction.

The separating agent for solid-phase extraction according to the present invention can widely be used in the concentration and/or removal of trace components and, in particular, they can be packed in a column or cartridge as shown in FIG. 1 prior to the practical use.

The column herein used comprises a hollow cylindrical body, both ends of which are sealed with column ends. As such a column end, there can be used a frit or a filter for the prevention of any outward flow of a gel and a liquid may pass through the column by directly communicating a connector and the column end. A cartridge is not equipped with any adapter required for letting a liquid flow through the column by nature. For this reason, the cartridge is used while attaching a specially designed member called cartridge holder, guard holder or adapter to a container.

Materials used for producing these columns and cartridges may be, for instance, inorganic materials such as stainless steel and glass; and synthetic resin materials such as polyethylene and polypropylene. The shape thereof may be, for instance, an injector having a volume ranging from 1 to 500 mL and preferably 1 to 100 mL.

In the column or cartridge for solid-phase extraction, porous plate-like members called frits or filters are fitted to the both ends thereof in order to prevent any outward flow of the separating agent packed therein during the solid-phase extraction operations. Materials for these frits and filters are not restricted to specific ones, but may be those produced from, for instance, stainless steel, glass, polyethylene and poly(tetrafluoroethylene).

The amount of the separating agent for solid-phase extraction to be packed in the reservoir of the column or cartridge may vary depending on factors such as the bulk density of the particles to be packed and the amount of a sample to be concentrated, but it in general ranges from 30 to 500 mg for the reservoir volume of 4 mL.

The applications of the column or cartridge packed with the separating agent for solid-phase extraction according to the present invention are not restricted to particularly ones, but the column or cartridge packed with the separating agent can, for instance, favorably be used for the purpose of concentrating a target substance present in, for instance, environment-related samples or medicine-related samples in a trace amount, when analyzing or treating these samples, or for the purpose of easily removing any impurity coexisting in these samples. The column or cartridge packed with the separating agent may likewise favorably be used for the determination of the content of any harmful substance such as an agricultural chemical present in the water samples derived from rivers or the like; the determination of the residual agricultural chemical in farm products; and the determination of the concentration of any drug present in sera, for instance, it is effective for the adsorption and/or removal of, for instance, proteins, but the applications thereof are not restricted to these specific ones at all.

The method for treating environment- or medicine-related samples according to the present invention comprises the step of solid-phase extracting a target component using the foregoing column or cartridge for solid-phase extraction which is packed with the foregoing separating agent for solid-phase extraction according to the present invention. The treating method comprises the step of concentrating a target substance present in a variety of samples in a trace amount or removing any impurity coexisting therein when analyzing these samples and accordingly, the treating method may be applied as a pre-treatment or a post-treatment for a variety of analyses.

EXAMPLES

The present invention will hereafter be described in more detail with reference to the following Examples, but the present invention is not restricted to these specific Examples at all.

Example 1

To a 1 L volume conical flask, there were added 50 g of silica gel having a particle size ranging from 35 to 65 µm (average particle: 50 µm) and 500 mL of a 0.2% (w/v) aqueous solution of hydroxypropyl cellulose (the hydroxypropyl cellulose was purchased from NACALAI TESQUE, INC.), followed by stirring the resulting mixture at 120 rpm and room temperature for 20 hours. After the completion of the agitation, the mixture was washed first with 900 mL of deionized water and then with 100 mL of acetone, followed by drying at 80° C. for 20 hours under reduced pressure to thus give silica gel particles coated with hydroxypropyl cellulose (hereafter referred to as "HPC Silica Gel").

To a 4-necked 100 mL volume flask, there were added 2.25 g of divinyl benzene having a purity of 80% (available from Aldrich Chemical Co., Ltd.), 0.75 g of styrene (available from Tokyo Kasei Kogyo Co., Ltd.) and 3 mL of toluene (available from Wako Pure Chemical Industries, Ltd.), followed by the dissolution thereof. In addition, there were added, to the resulting mixture, 60 mL of a 0.2% (w/v) aqueous solution of methyl cellulose (the methyl cellulose was purchased from NACALAI TESQUE, INC.) and 0.75 mL of a 10% (w/v) aqueous solution of sodium dodecyl benzene sulfate (the sodium dodecyl benzene sulfate was a product manufactured by Wako Pure Chemical Industries, Ltd.), followed by stirring the mixture at 500 rpm for 10 minutes. After completing the agitation of the mixture, there was added, to the mixture 1.5 mL of a 1% (w/v) toluene solution of 2,2'-azobis-isobutyronitrile (this 2,2'-azobis-isobutyronitrile was a product manufactured by Wako Pure Chemical Industries, Ltd.), followed by stirring the mixture at 500 rpm for 10 minutes. After the confirmation of whether an emulsion was formed or not, the emulsion was stirred at 100 rpm, 4.0 g of the foregoing HPC Silica Gel was added to the emulsion and the reaction was carried out at 80° C. for 20 hours.

After the completion of the reaction, the reaction system was washed, in order, with 300 mL of methanol, 350 mL of deionized water and 50 mL of acetone, followed by drying at 80° C. for 20 hours under reduced pressure. The resulting particles were classified to give a particulate product having a particle size ranging from 38 to 75 µm using an electromagnetic classification-oscillator (OCTAGON DIGITAL available from SEISHIN ENTERPRISE CO., LTD.).

Comparative Example 1

Monomers having the same mixing ratio used in Example 1 were subjected to the suspension polymerization according to the same procedures used in Example 1 except that the HPC Silica Gel and sodium dodecyl benzene sulfate were not added and then the resulting product was washed to give styrene-divinyl benzene copolymer particles. After drying the particles, they were classified into particles having a particle size ranging from 38 to 75 µm to thus give a separating agent for solid-phase extraction.

Evaluation According to Evaluation Condition 1

The particles prepared in Example 1 (70 mg) and Comparative Example 1 (50 mg) and classified in such a manner that they had a particle size ranging from 38 to 75 µm were packed in reservoirs each having a volume of 4 mL to thus give each corresponding cartridge for solid-phase extraction and each cartridge was inspected for the recovery rate according to the following procedures:
(1) Each cartridge for solid-phase extraction was fitted to a syringe adapter;
(2) Methanol (1 mL) was passed through the cartridge at a flow rate of 1 mL/min;
(3) A 50 mM sodium phosphate buffer solution (pH 6.0, 1 mL) was passed through the cartridge at a flow rate of 1 mL/min;
(4) A product obtained by dissolving 10 µg of caffeine, 10 µg of ketoprofen and 20 µg of p-toluidine in 1 mL of a 50 mM sodium phosphate buffer solution (pH 6.0) containing 10 mg of BSA (bovine serum albumin) was passed through the cartridge at a flow rate of 1 mL/min, to thus make the sample adsorb on the particles contained in the cartridge for solid-phase extraction;
(5) A 50 mM sodium phosphate buffer solution (pH 6.0, 1 mL) containing 5% methanol was passed through the cartridge at a flow rate of 1 mL/min to thus wash the same;
(6) Methanol (1 mL) was passed through the cartridge at a flow rate of 1 mL/min to thus recover the eluate;
(7) An aliquot of 20 µL was taken from the eluate thus recovered and analyzed by a high performance liquid chromatograph (LC-2010C HT, available from Shimadzu Corporation) to thus determine the area;
(8) Conditions for the Determination:
Column: STR ODS-II4, 6 mmφ×150 mm (available from Shinwa Chemical Industries, Ltd.);
Mobile phase: 20 mM sodium phosphate buffer (pH 7.0)/acetonitrile=80/20→75/25 (after 5 minutes);
Flow Rate, 1.0 mL/min; Detector: UV-absorbing detector;
Wavelength: UV 254 nm; Amount of Sample to be Injected: 20 µL.

The results thus obtained are summarized in the following Table 1:

TABLE 1

(Test Results obtained under Evaluation Condition 1)

| | Rate of Recovery (%) | |
|---|---|---|
| | Example 1 | Comp. Example 1 |
| Caffeine | 109.2 | 105.3 |
| Ketoprofen | 85.1 | 91.5 |
| p-Toluidine | 103.4 | 102.1 |

The separating agent prepared in Example 1 was thus found to be an excellent separating agent for solid-phase extraction since it permitted the achievement of a high rate of recovery on the order of not less than 85%. On the contrary, the separating agent prepared in Comparative Example 1 was found to have slightly low rates of recovery for caffeine and p-toluidine which are highly soluble in water as compared with ketoprofen. On the other hand, the both separating agents prepared in Example 1 and Comparative Example 1 permitted the removal of almost 99% of BSA.

Evaluation According to Evaluation Condition 2

The particles prepared in Example 1 (70 mg) and Comparative Example 1 (50 mg) and classified such that they had a particle size ranging from 38 to 75 µm were packed in reservoirs each having a volume of 4 mL to thus give each corresponding cartridge for solid-phase extraction and each cartridge was inspected for the recovery rate according to the following procedures:
(1) Each cartridge for solid-phase extraction was fitted to a syringe adapter;
(2) Methanol (1 mL) was passed through the cartridge at a flow rate of 1 mL/min;
(3) A 20 mM sodium phosphate buffer solution (pH 7.0, 1 mL) was passed through the cartridge at a flow rate of 1 mL/min;
(4) A product obtained by dissolving 10 µg of procaine-amide and 20 µg of theophylline in 1 mL of a 20 mM sodium phosphate buffer solution (pH 7.0) containing 10 mg of BSA (bovine serum albumin) was passed through the cartridge at a flow rate of 1 mL/min, to thus make the sample adsorb on the particles contained in the cartridge for solid-phase extraction;
(5) A 20 mM sodium phosphate buffer solution (pH 7.0, 1 mL) was passed through the cartridge at a flow rate of 1 mL/min to thus wash the same;
(6) An eluting solution comprising a 20 mM sodium phosphate buffer solution (pH 6.0)/methanol=50:50 (1 mL) was passed through the cartridge at a flow rate of 1 mL/min and the resulting eluate was thus recovered;
(7) An aliquot of 20 µL was taken from the eluate thus recovered and analyzed by a high performance liquid chromatograph (LC-2010C HT, purchased from Shimadzu Corporation) to thus determine the area;
(8) Conditions for the Determination:
Column: Asahipak ODP-50 4D, 4.6 mmφ×150 mm (available from Showa Denko K.K.); Mobile phase: 20 mM sodium phosphate buffer (pH 10.0)/acetonitrile=90/10→70/30 (after 5 minutes);
Flow Rate: 0.6 mL/min; Detector: UV-absorbing detector;
Wavelength: UV 273 nm; Amount of Sample to be injected: 20 µL.

The results thus obtained are summarized in the following Table 2:

TABLE 2

(Test Results obtained under Evaluation Condition 2)

| | Rate of Recovery (%) | |
|---|---|---|
| | Example 1 | Comp. Example 1 |
| Theophylline | 94.1 | 84.0 |
| Procaine-amide | 102.7 | 96.3 |

The separating agent prepared in Example 1 was thus found to be an excellent separating agent for solid-phase extraction since it permitted the achievement of a high rate of recovery on the order of not less than 85%. On the contrary, the separating agent prepared in Comparative Example 1 was found to have rates of recovery for water-soluble drugs, or theophylline and procaine-amide lower than those observed for the separating agent prepared in Example 1. On the other hand, the both separating agents prepared in Example 1 and Comparative Example 1 permitted the removal of almost 99% of BSA.

Example 2

To a 1 L volume conical flask, there were added 50 g of silica gel having an average particle size of 50 μm and 600 mL of a 1.0% (w/v) aqueous solution of polyvinyl alcohol (this PVA was a product available from JAPAN VAM & POVAL CO., LTD. and having a degree of saponification ranging from 78.0 to 80.5 mole %), followed by stirring at 120 rpm for not less than 20 hours at room temperature. After the completion of the agitation, the resulting mixture was washed with 1300 mL of deionized water and then with 100 mL of acetone and then dried at 80° C. under reduced pressure to thus give silica gel particles coated with polyvinyl alcohol layer (hereafter referred to as "PVA Silica Gel"). Yield: 87.9% (49.25 g).

To a 4-necked 100 mL volume flask, there were added 1.0 g of divinyl benzene having a purity of 80% (available from Aldrich Chemical Co., Ltd.), 0.5 g of ethylene glycol dimethacrylate (available from Wako Pure Chemical Industries, Ltd.), 0.5 g of N-vinyl pyrrolidone (available from NACALAI TESQUE, INC.) and 2 mL of toluene (available from Wako Pure Chemical Industries, Ltd.) in a nitrogen gas atmosphere at room temperature, followed by the dissolution thereof. Further, there were added, to the resulting mixture, 40 mL of a 1.0% (w/v) aqueous solution of polyvinyl alcohol (this PVA was a product available from JAPAN VAM & POVAL CO., LTD.) and 0.5 mL of a 10% (w/v) aqueous solution of sodium dodecyl benzene sulfate (this sodium dodecyl benzene sulfate was a product manufactured by Wako Pure Chemical Industries, Ltd.), followed by stirring at 500 rpm for 10 minutes. After the completion of the agitation, there was added, to the mixture, 1 mL of a 1% (w/v) toluene solution of 2,2'-azobis-isobutyronitrile (this 2,2'-azobis-isobutyronitrile was a product manufactured by Wako Pure Chemical Industries, Ltd.), followed by stirring at 500 rpm for 10 minutes. After the confirmation of whether an emulsion was formed or not, the emulsion was stirred at 100 rpm, 8.0 g of the foregoing PVA Silica Gel was added to the emulsion and the reaction was carried out at 80° C. for not less than 6 hours.

After the completion of the reaction, the reaction system was washed, in order, with 300 mL of methanol, 250 mL of deionized water and 50 mL of acetone, followed by drying at 80° C. under reduced pressure. The resulting particles were classified to give a particulate product having a particle size ranging from 38 to 75 μm.

Example 3

To a 1 L volume conical flask, there were added 50 g of silica gel having an average particle size of 50 μm and 600 mL of a 0.2% (w/v) aqueous solution of methyl cellulose (this methyl cellulose was purchased from NACALAI TESQUE, INC.), followed by stirring at 120 rpm for not less than 20 hours at room temperature. After the completion of the agitation, the resulting mixture was washed with 1300 mL of deionized water and then with 100 mL of acetone and then dried at 80° C. under reduced pressure to thus give silica gel particles coated with methyl cellulose layer (hereafter referred to as "MC Silica Gel"). Yield: 89.9% (46.06 g).

To a 4-necked, 100 mL-volume flask, there were added 1.0 g of divinyl benzene having a purity of 80% (available from Aldrich Chemical Co., Ltd.), 0.5 g of ethylene glycol dimethacrylate (available from Wako Pure Chemical Industries, Ltd.), 0.5 g of N-vinyl pyrrolidone (available from NACALAI TESQUE, INC.) and 2 mL of toluene (available from Wako Pure Chemical Industries, Ltd.) in a nitrogen gas atmosphere at room temperature, followed by the dissolution thereof. Further, there were added, to the resulting mixture, 40 mL of a 0.2% (w/v) aqueous solution of methyl cellulose and 0.5 mL of a 10% (w/v) aqueous solution of sodium dodecyl benzene sulfate (this sodium dodecyl benzene sulfate was a product manufactured by Wako Pure Chemical Industries, Ltd.), followed by stirring at 500 rpm for 10 minutes. After the completion of the agitation, there was added, to the mixture, 1 mL of a 1% (w/v) toluene solution of 2,2'-azobis-isobutyronitrile (this 2,2'-azobis-isobutyronitrile was a product available from Wako Pure Chemical Industries, Ltd.), followed by stirring at 500 rpm for 10 minutes. After the confirmation of whether an emulsion was formed or not, the emulsion was stirred at 100 rpm, 8.0 g of the foregoing MC Silica Gel was added to the emulsion and the reaction was carried out at 80° C. for not less than 6 hours.

After the completion of the reaction, the reaction system was washed, in order, with 500 mL of methanol, 500 mL of deionized water and 100 mL of acetone, followed by drying at 80° C. under reduced pressure. The resulting particles were classified to give a particulate product having a particle size ranging from 38 to 75 μm.

Example 4

To a 1 L volume conical flask, there were added 30 g of silica gel having an average particle size of 50 μm and 360 mL of a 0.2% (w/v) methanol solution of ethyl cellulose (this ethyl cellulose was purchased from NACALAI TESQUE, INC.), followed by stirring at 120 rpm for not less than 20 hours at room temperature. After the completion of the agitation, the resulting mixture was washed with 600 mL of deionized water, 200 mL of methanol and 50 mL of acetone and then dried at 80° C. under reduced pressure to thus give silica gel particles coated with ethyl cellulose layer (hereafter referred to as "EC Silica Gel"). Yield: 87.3% (26.83 g).

To a 4-necked, 100 mL-volume flask, there were added 1.0 g of divinyl benzene having a purity of 80% (available from Aldrich Chemical Co., Ltd.), 0.5 g of ethylene glycol dimethacrylate (available from Wako Pure Chemical Industries, Ltd.), 0.5 g of N-vinyl pyrrolidone (available from NACALAI TESQUE, INC.) and 2 mL of toluene (available from Wako Pure Chemical Industries, Ltd.) in a nitrogen gas atmosphere at room temperature, followed by the dissolution thereof. Further, there were added, to the resulting mixture, 40 mL of a 0.2% (w/v) aqueous solution of methyl cellulose and 0.5 mL of a 10% (w/v) aqueous solution of sodium dodecyl benzene sulfate (this sodium dodecyl benzene sulfate was a product manufactured by Wako Pure Chemical Industries, Ltd.), followed by stirring at 500 rpm for 10 minutes. After the completion of the agitation, there was added, to the mixture, 1 mL of a 1% (w/v) toluene solution of 2,2'-azobis-isobutyronitrile (this 2,2'-azobis-isobutyronitrile was a product available from Wako Pure Chemical Industries, Ltd.), followed by stirring at 500 rpm for 10 minutes. After the confirmation of whether an emulsion was formed or not, the emulsion was stirred at 100 rpm, 8.0 g of the foregoing EC Silica Gel was added to the emulsion and the reaction was carried out at 80° C. for not less than 6 hours.

After the completion of the reaction, the reaction system was washed, in order, with 300 mL of methanol, 250 mL of deionized water and 50 mL of acetone, followed by drying at 80° C. under reduced pressure. The resulting particles were classified to give a particulate product having a particle size ranging from 38 to 75 μm.

Example 5

To a 1 L volume conical flask, there were added 30 g of silica gel having an average particle size of 50 μm and 360 mL of a 0.2% (w/v) aqueous solution of hydroxypropyl cellulose (this hydroxypropyl cellulose was purchased from NACALAI TESQUE, INC.), followed by stirring at 120 rpm for not less than 20 hours at room temperature. After the completion of the agitation, the resulting mixture was washed with 800 mL of deionized water and 50 mL of acetone and then dried at 80° C. under reduced pressure to thus give silica gel particles coated with hydroxypropyl cellulose layer (hereafter referred to as "HPC Silica Gel"). Yield: 89.5% (27.50 g).

To a 4-necked, 100 mL-volume flask, there were added 1.0 g of divinyl benzene having a purity of 80% (available from Aldrich Chemical Co., Ltd.), 0.5 g of ethylene glycol dimethacrylate (available from Wako Pure Chemical Industries, Ltd.), 0.5 g of N-vinyl pyrrolidone (available from NACALAI TESQUE, INC.) and 2 mL of toluene (available from Wako Pure Chemical Industries, Ltd.) in a nitrogen gas atmosphere at room temperature, followed by the dissolution thereof. Further, there were added, to the resulting mixture, 40 mL of a 0.2% (w/v) aqueous solution of methyl cellulose and 0.5 mL of a 10% (w/v) aqueous solution of sodium dodecyl benzene sulfate (this sodium dodecyl benzene sulfate was a product manufactured by Wako Pure Chemical Industries, Ltd.), followed by stirring at 500 rpm for 10 minutes. After the completion of the agitation, there was added, to the mixture, 1 mL of a 1% (w/v) toluene solution of 2,2'-azobis-isobutyronitrile (this 2,2'-azobis-isobutyronitrile was a product available from Wako Pure Chemical Industries, Ltd.), followed by stirring at 500 rpm for 10 minutes. After the confirmation of whether an emulsion was formed or not, the emulsion was stirred at 100 rpm, 8.0 g of the foregoing HPC Silica Gel was added to the emulsion and the reaction was carried out at 80° C. for not less than 6 hours.

After the completion of the reaction, the reaction system was washed, in order, with 300 mL of methanol, 250 mL of deionized water and 50 mL of acetone, followed by drying at 80° C. under reduced pressure. The resulting particles were classified into a particulate product having a particle size ranging from 38 to 75 μm.

Evaluation According to Evaluation Condition 3

The particles (70 mg each) prepared in Examples 2 to 5 and classified such that they had a particle size ranging from 38 to 75 μm were packed in reservoirs each having a volume of 4 mL to thus give each corresponding cartridge for solid-phase extraction and each cartridge was inspected for the recovery rate according to the following procedures. The results thus obtained are summarized in the following Table 3:

(1) Each cartridge for solid-phase extraction was fitted to a syringe adapter;
(2) Methanol (1 mL) was passed through the cartridge at a flow rate of 1 mL/min;
(3) A 50 mM sodium phosphate buffer solution (pH 6.0, 1 mL) was passed through the cartridge at a flow rate of 1 mL/min;
(4) A product obtained by dissolving 0.6 μg of procaine-amide and 0.6 μg of theophylline in 2 mL of a 50 mM sodium phosphate buffer solution (pH 6.0) containing 20 mg of BSA (bovine serum albumin) was passed through the cartridge at a flow rate of 1 mL/min, to thus make the sample adsorb on the particles contained in the cartridge for solid-phase extraction;
(5) A 50 mM sodium phosphate buffer solution (pH 6.0, 1 mL) was passed through the cartridge at a flow rate of 1 mL/min to thus wash the same;
(6) Methanol (1 mL) was passed through the cartridge at a flow rate of 1 mL/min and the resulting eluate was thus recovered;
(7) An aliquot of 20 μL was taken from the eluate thus recovered and analyzed by a high performance liquid chromatograph (LC-2010C HT, purchased from Shimadzu Corporation) to thus determine the area;
(8) Conditions for the Determination:
Column: Asahipak ODP-50 4D, 4.6 mmϕ×150 mm (available from Showa Denko K.K.); Mobile phase: 20 mM sodium phosphate buffer solution (pH 10.0)/acetonitrile=90/10→70/30 (after 5 minutes);
Flow Rate: 0.6 mL/min; Detector: UV-absorbing detector;
Wavelength: UV 273 nm; Amount of Sample to be injected: 20 μL.

TABLE 3

(Test Results obtained under Evaluation Condition 3)

| | Rate of Recovery (%) | |
|---|---|---|
| | Theophylline | Procaine-amide |
| Example 2 | 6.3 | 62.7 |
| Example 3 | 50.1 | 73.1 |
| Example 4 | 48.5 | 58.6 |
| Example 5 | 56.5 | 75.7 |

The product prepared in Example 2 comprising the PVA-coated core particles showed an extremely low recovery rate of theophylline, while the products comprising the cellulose derivative-coated core particles showed high recovery rates thereof as compared with the product of Example 2. Among the products comprising the cellulose derivative-coated core particles, the product prepared in Example 5 comprising the hydroxypropyl cellulose-coated core particles showed a recovery rates for the both theophylline and procaine-amide substantially higher than those observed for the products prepared in Examples 3 and 4. Accordingly, it is considered that the core particles are well-coated with a polymer serving as the medium for solid-phase extraction in the product of Example 5.

Example 6

To a 4-necked, 100 mL-volume flask, there were added 1.5 g of divinyl benzene having a purity of 80% (available from Aldrich Chemical Co., Ltd.), 0.75 g of ethylene glycol di-methacrylate (available from Wako Pure Chemical Industries, Ltd.), 0.75 g of N-vinyl pyrrolidone (available from NACALAI TESQUE, INC.) and 3 mL of toluene (available from Wako Pure Chemical Industries, Ltd.) in a nitrogen gas atmosphere at room temperature, followed by the dissolution thereof. Further, there were added, to the resulting mixture, 60 mL of a 0.2% (w/v) aqueous solution of methyl cellulose and 0.75 mL of a 10% (w/v) aqueous solution of sodium dodecyl benzene sulfate (this sodium dodecyl benzene sulfate was a product manufactured by Wako Pure Chemical Industries, Ltd.), followed by stirring at 500 rpm for 10 minutes. After the completion of the agitation, there was added, to the mixture, 1.5 mL of a 1% (w/v) toluene solution of 2,2'-azobis-isobutyronitrile (this 2,2'-azobis-isobutyronitrile was a product available from Wako Pure Chemical Industries, Ltd.), followed by stirring at 500 rpm for 10 minutes. After the confirmation of whether an emulsion was formed or not, the emulsion was stirred at 100 rpm, 6.0 g of the foregoing HPC Silica Gel prepared in Example 5 was added to the emulsion and the reaction was carried out at 80° C. for not less than 20 hours.

After the completion of the reaction, the reaction system was washed, in order, with 300 mL of methanol, 250 mL of deionized water and 50 mL of acetone, followed by drying at 80° C. under reduced pressure. The resulting particles were classified into a particulate product having a particle size ranging from 38 to 75 μm.

Example 7

To a 1 L volume conical flask, there were added 50 g of silica gel having an average particle size of 50 μm and 500 mL of a 0.2% (w/v) aqueous solution of hydroxypropyl cellulose (this hydroxypropyl cellulose was purchased from NACALAI TESQUE, INC.), followed by stirring at 120 rpm for not less than 20 hours at room temperature. After the completion of the agitation, the resulting mixture was washed with 900 mL of deionized water and 100 mL of acetone and then dried at 80° C. under reduced pressure to thus give silica gel particles coated with hydroxypropyl cellulose layer hereafter referred to as "HPC Silica Gel"). Yield: 88.8% (45.28 g).

To a 4-necked, 100 mL-volume flask, there were added 1.5 g of divinyl benzene having a purity of 80% (available from Aldrich Chemical Co., Ltd.), 0.75 g of ethylene glycol di-methacrylate (available from Wako Pure Chemical Industries, Ltd.), 0.75 g of N-vinyl pyrrolidone (available from NACALAI TESQUE, INC.) and 3 mL of toluene (available from Wako Pure Chemical Industries, Ltd.) in a nitrogen gas atmosphere at room temperature, followed by the dissolution thereof Further, there were added, to the resulting mixture, 60 mL of a 0.2% (w/v) aqueous solution of methyl cellulose and 0.75 mL of a 10% (w/v) aqueous solution of sodium dodecyl benzene sulfate (this sodium dodecyl benzene sulfate was a product manufactured by Wako Pure Chemical Industries, Ltd.), followed by string at 500 rpm for 10 minutes. After the completion of the agitation, there was added, to the mixture, 1.5 mL of a 1% (w/v) toluene solution of 2,2'-azobis-isobutyronitrile (this 2,2'-azobis-isobutyronitrile was a product available from Wako Pure Chemical Industries, Ltd.), followed by stirring at 500 rpm for 10 minutes. After the confirmation of whether an emulsion was formed or not, the emulsion was stirred at 100 rpm, 4.0 g of the foregoing HPC Silica Gel was added to the emulsion and the reaction was carried out at 80° C. for not less than 20 hours.

After the completion of the reaction, the reaction system was washed, in order, with 300 mL of methanol, 250 mL of deionized water and 50 mL of acetone, followed by drying at 80° C. under reduced pressure. The resulting particles were classified into a particulate product having a particle size ranging from 38 to 75 μm.

Yield observed prior to the classification: 89.3% (6.25 g);
Yield observed after the classification: 73.4% (5.14 g).

Comparative Example 2

Monomers having the same mixing ratio used in Example 3 were subjected to the suspension polymerization according to the same procedures used in Example 3 except that silica gel and sodium dodecyl benzene sulfate were not added and then the resulting product was washed to give ethylene glycol di-methacrylate/N-vinyl pyrrolidone/divinyl benzene copolymer particles After drying the particles, they were classified into particles having a particle size ranging from 38 to 75 μm.

Yield observed prior to the classification: 73.5% (14.71 g);
Yield observed after the classification: 15.4% (3.09 g).

Evaluation According to Evaluation Condition 4

The particles prepared in Example 3, Example 6 and Example 7 (70 mg each) and comparative Example 2 (50 mg) and classified such that they had a particle size ranging from 38 to 75 μm were packed in reservoirs each having a volume of 4 mL to thus give each corresponding cartridge for solid-phase extraction. Each cartridge was inspected for the recovery rate according to the following procedures. In the following evaluation condition 4, the concentrations of the drugs used were higher than those used in the evaluation condition 3. The results thus obtained are summarized in the following Table 4:

(1) Each cartridge for solid-phase extraction was fitted to a syringe adapter;
(2) Methanol (1 mL) was passed through the cartridge at a flow rate of 1 mL/min;
(3) A 50 mM sodium phosphate buffer solution (pH 6.0, 1 mL) was passed through the cartridge at a flow rate of 1 mL/min;
(4) A product obtained by dissolving 20 g of procaine-amide and 40 μg of theophylline in 1 mL of a 50 mM sodium phosphate buffer solution (pH 6.0) containing 20 mg of BSA (bovine serum albumin) was passed through the cartridge at a flow rate of 1 mL/min, to thus make the sample adsorb on the particles contained in the cartridge for solid-phase extraction;
(5) A 50 mM sodium phosphate buffer solution (pH 6.0, 1 mL) was passed through the cartridge at a flow rate of 1 mL/min to thus wash the same;
(6) Methanol (1 mL) was passed through the cartridge at a flow rate of 1 mL/min and the resulting eluate was thus recovered;
(7) An aliquot of 20 μL was taken from the eluate thus recovered and analyzed by a high performance liquid chromatograph (LC-2010C HT, purchased from Shimadzu Corporation) to thus determine the area;
(8) Conditions for the Determination:
Column: Asahipak ODP-50 4D, 4.6 mmφ×150 mm (available from Showa Denko K.K.); Mobile phase: 20 mM sodium phosphate buffer (pH 10.0)/acetonitrile=90/10→70/30 (after 5 minutes);
Flow Rate: 0.6 mL/min; Detector: UV-absorbing detector;
Wavelength: UV 273 nm; Amount of Sample to be injected: 20 μL.

The results thus obtained are summarized in the following Table 4:

TABLE 4

(Test Results obtained under Evaluation Condition 4)

| | Rate of Recovery (%) | |
|---|---|---|
| | Theophylline | Procaine-amide |
| Example 3 | 21.8 | 36.4 |
| Example 6 | 79.9 | 70.6 |
| Example 7 | 94.6 | 84.9 |
| Comparative Example 2 | 98.2 | 91.9 |

All of the separating agents prepared in Example 3, Example 6 and Example 7 and Comparative Example 2 permitted the removal of almost 99% of BSA.

The separating agent of Example 3 comprises the methyl cellulose-coated core particles, but the ratio (by mass) of the monomer to silica gel is 0.25. The ratios are 0.5 for the agent of Example 6 and 0.75 for the agent of Example 7. The separating agent of Example 3 shows a low recovery rate and this would be possibly due to the small amount of the coated polymer serving as the solid-phase extraction medium. The particles of Comparative Example 2 consisting only of the polymer show an excellent recovery rate, but the product of Example 7 likewise recovers the drugs sufficiently.

Example 8

The particles prepared in Example 1 and classified into a particulate product having a particle size ranging from 38 to 75 μm were packed in a stainless steel cartridge having a size of 4.6 mmφ×10 mm and then the cartridge thus packed with the particles was secured to a stainless steel cartridge holder to thus give a column for solid-phase extraction. The resulting column was inspected for the recovery rate according to the following procedures:

(1) The column for solid-phase extraction was connected to a column-switching device (NANO SPACE SI-2 available from Shiseido Co., Ltd.) through a high-pressure six-way switching valve;

(2) A 20 mM sodium phosphate buffer solution (pH 7.0) was passed through the column at a flow rate of 1 mL/min for 4 minutes to thus condition the column;

(3) A product obtained by dissolving 3.5 μg of procaine-amide and 7 μg of theophylline in 350 μL of a 20 mM sodium phosphate buffer solution (pH 7.0) containing 3.5 mg of BSA (bovine serum albumin) was passed through the column at a flow rate of 1 mL/min for one minute, to thus make the sample adsorb on the column for solid-phase extraction;

(4) An eluting solution consisting of 20 mM sodium phosphate buffer solution (pH 6.0)/methanol=80/20 was passed through the column at a flow rate of 0.5 mL/min for 2 minutes and the resulting eluate was recovered;

(5) An aliquot of 20 μL was taken from the eluate thus recovered and analyzed by a high performance liquid chromatograph (LC-2010C HT, purchased from Shimadzu Corporation) to thus determine the area;

(6) A 20 mM sodium phosphate buffer solution (pH 7.0) was passed through the column at a flow rate of 1.0 mL/min for 4 minutes to thus wash and condition the column;

(7) The solid-phase extraction operations were repeated 100 times while using the foregoing column-switching device to thus conduct the desired tests;

(8) Conditions for the Determination:

Column: Asahipak ODP-50 4D, 4.6 mmφ×150 mm (available from Showa Denko K.K.); Mobile phase: 20 mM sodium phosphate buffer solution (pH 10.0)/acetonitrile=90/10→70/30 (after 5 minutes);

Flow Rate: 0.6 mL/min; Detector: UV-absorbing detector; Wavelength: UV 273 nm; Amount of Sample to be Injected: 20 μL.

The results thus obtained are summarized in the following Table 5:

TABLE 5

(Test Results obtained under Evaluation Condition 5)

| | Example 8 (n = 100) | |
|---|---|---|
| | Recovery Rate (%) | Coefficient of variation (%) |
| Procaine-amide | 100.9 | 2.2 |
| Theophylline | 90.6 | 2.7 |

The product prepared in Example 8 was found to be an excellent separating agent for solid-phase extraction since it showed a recovery rate of not less than 90% and a coefficient of variation of less than 3%. In addition, the solid-phase extraction operations were repeated 100 times using the column for solid-phase extraction. As a result, it was found that the column did not undergo any quality deterioration and that the column was also excellent in the durability.

What is claimed is:

1. A separating agent, comprising:
   a core particle of a base material;
   a hydrophilic polymer layer on the surface of the particles; and
   a hydrophobic polymer layer on the surface of the hydrophilic polymer layer.

2. The separating agent of claim 1, wherein the hydrophilic polymer layer comprises a hydrophilic polymer and the hydrophilic polymer is at least one member selected from the group consisting of hydroxypropyl cellulose, methyl cellulose and ethyl cellulose.

3. The separating agent of claim 1, wherein the hydrophobic polymer layer comprises a hydrophobic polymer which is selected from the group consisting of a polymer of a hydrophobic, crosslinkable monomer (A); a copolymer of a hydrophobic, crosslinkable monomer (A) and a hydrophobic, non-crosslinkable monomer (B); a copolymer of a hydrophobic, crosslinkable monomer (A) and a hydrophilic monomer (C); and a copolymer of a hydrophobic, crosslinkable monomer (A), a hydrophobic, non-crosslinkable monomer (B) and a hydrophilic monomer (C).

4. The separating agent of claim 3, wherein the hydrophobic, crosslinkable monomer (A) is at least one member selected from the group consisting of a di-(meth)acrylic acid ester, a poly(meth)acrylic acid ester of a polyhydric alcohol, and an aromatic compound comprising at least two vinyl groups.

5. The separating agent of claim 3, wherein the hydrophobic, non-crosslinkable monomer (B) is at least one member selected from the group consisting of a (meth)acrylic acid ester, a vinyl carboxylate and a styrenic monomer.

6. The separating agent of claim 3, wherein the hydrophilic monomer (C) is at least one member selected from the group consisting of a hydroxyl group substituted (meth)acrylic acid ester, a (meth)acrylamide, and a N-vinyl pyrrolidone.

7. The separating agent of claim 3, wherein the hydrophobic, crosslinkable monomer (A) is di-vinyl benzene.

8. The separating agent of claim 3, wherein the hydrophobic, non-crosslinkable monomer (B) is styrene.

9. The separating agent of claim 1, wherein a total amount of the hydrophobic polymer layer ranges from 5 to 500 parts by mass, per 100 parts by mass of a total amount of the core particles and the hydrophilic polymer layer.

10. The separating agent of claim 1, wherein the core particle is at least one member selected from the group consisting of a silica gel particle, a cellulose particle, an agarose particle, a ceramic particle, a carbon particle and a synthetic polymer particle.

11. The separating agent of claim 1, wherein an average particle size is in the range from 1 to 200 μm.

* * * * *